US007601365B2

(12) United States Patent
Nayeri (10) Patent No.: US 7,601,365 B2
(45) Date of Patent: Oct. 13, 2009

(54) SYNERGETIC EFFECTS OF HGF AND ANTIBACTERIAL TREATMENT

(75) Inventor: Fariba Nayeri, Linköping (SE)

(73) Assignee: Damavand Wound, AB, Linkoping (SE)

( * ) Notice: Subject to any disclaimer, the term of this patent is extended or adjusted under 35 U.S.C. 154(b) by 952 days.

(21) Appl. No.: 10/398,304

(22) PCT Filed: Aug. 28, 2001

(86) PCT No.: PCT/SE01/01831

§ 371 (c)(1),
(2), (4) Date: Apr. 2, 2003

(87) PCT Pub. No.: WO02/17964

PCT Pub. Date: Mar. 7, 2002

(65) Prior Publication Data

US 2004/0042968 A1    Mar. 4, 2004

(30) Foreign Application Priority Data

Aug. 28, 2000  (SE) .................................... 0003038
May 21, 2001   (SE) .................................... 0101823

(51) Int. Cl.
*A61F 13/02* (2006.01)
(52) U.S. Cl. .................................... 424/443
(58) Field of Classification Search ........................ None
See application file for complete search history.

(56) References Cited

U.S. PATENT DOCUMENTS

| 5,004,805 | A |   | 4/1991  | Gohda et al. |
| 5,342,831 | A | * | 8/1994  | Nakamura et al. ............ 514/12 |
| 5,648,273 | A |   | 7/1997  | Bottaro et al. |
| 5,656,443 | A |   | 8/1997  | Goldberg et al. |
| 5,776,464 | A |   | 7/1998  | Nakamura |
| 5,827,673 | A |   | 10/1998 | Matsumori |
| 5,840,311 | A |   | 11/1998 | Nakamura et al. |
| 5,855,918 | A | * | 1/1999  | Mrsny et al. ................ 424/530 |
| 5,977,310 | A |   | 11/1999 | Namiki et al. |
| 6,036,972 | A |   | 3/2000  | Nakamura et al. |
| 6,303,126 | B1 |  | 10/2001 | Nakamura et al. |
| 6,756,358 | B2 |  | 6/2004  | Iwamoto et al. |
| 2003/0176347 | A1 | | 9/2003 | Nakamura et al. |

FOREIGN PATENT DOCUMENTS

| EP | 462549 | 12/1991 |
| EP | 722737 | 7/1996 |
| EP | 724884 | 8/1996 |

(Continued)

OTHER PUBLICATIONS

NPUAP Report_Jul. 29, 2000.*
Hepatocyte Growth Factor (HGF) in Patients with Pneumonia: A Comparison Between Survivors and Non-Survivors; Nayeri, et al, 1998 Scandinavian University Press. ISSN 0036-5548; Scand J. Infec Dis 30; 405-409, 1998.
Shiota et al, "Hepatocyte growth factor inhibits growth of hepatocellular carcinoma cells", *Proc. Natl. Acad. Sci.*, vol. 89, pp. 373-377, Jan. 1992.

(Continued)

*Primary Examiner*—Carlos A. Azpuru
(74) *Attorney, Agent, or Firm*—Porter Wright Morris & Arthur LLP (57) ABSTRACT

Methods of treating a skin ulcer of a mammal comprise providing an antibiotic or fungicide, and HGF to said mammal. Additional methods of treating a mammal with a skin ulcer comprise identifying a mammal with a skin ulcer as one in need of an antibiotic and HGF, and providing an antibiotic and HGF to the identified mammal.

25 Claims, 6 Drawing Sheets

FOREIGN PATENT DOCUMENTS

| | | |
|---|---|---|
| EP | 784980 | 7/1997 |
| EP | 847757 | 6/1998 |
| EP | 890361 | 1/1999 |
| EP | 1074264 | 2/2001 |
| JP | 8268907 | 10/1996 |
| WO | 93 06853 | 4/1993 |
| WO | 94 04175 | 3/1994 |
| WO | 80 35968 | 2/1996 |
| WO | 96 05855 | 2/1996 |
| WO | WO 96/41818 | 12/1996 |
| WO | 98 24467 | 6/1998 |
| WO | 98 41227 | 9/1998 |
| WO | 99 55361 | 11/1999 |
| WO | WO 01/44294 * | 6/2001 |
| WO | 02 22162 | 3/2002 |

OTHER PUBLICATIONS

Brzozowski et al, "Involvement of Cycclooxygenase (Cox)-2 Products in Acceleration of Ulcer Healing by Gastrin and Hepatocyte Growth Factor", *Journal of Physiology and Pharmacology*, 2000, 51, 4, pp. 751-773.

Morishita et al, "Therapeutic Angiogenesis Induced by Human Recombinant Hepatocyte Growth Factor in Rabbit Hind Limb Ischemia Model as Cytokine Supplement Therapy", *Hypertension*, Jun. 1999, pp. 1379-1384.

Takahashi et al, "Hepatocyte Growth Factor as a Key to Modulate Anti-Ulcer Action of Prostaglandins in Stomach", *J. Clin. Invest.*, vol. 98, No. 11, Dec. 1996, pp. 2604-2611.

Tashiro et al, "Deduced primary structure of rat hepatocyte growth factor and expression of the mRNA in rat tissues", *Proc. Natl. Acad. Sci.*, vol. 87, pp. 3200-3204, Apr. 1990.

Taipale et al, "Hepatocyte Growth Factor Releases Epithelial and Endothelial Cells from Growth Arrest Induced by Transforming Growth Factor-$\beta1$", *The Journal of Biological Chemistry*, vol. 271, No. 8, Feb. 23, 1996, pp. 4342-4348.

Nayeri et al, "Hepatocyte Growth Factor Levels in Cerebrospinal Fluid: A Comparison Between Acute Bacterial and Nonbacterial Meningitis", *The Journal of Infectious Diseases*, 2000; 181, pp. 2092-2094.

Gohda et al, "Purification and Partial Characterization of Hepatocyte Growth Factor from Plasma of a Patient with Fulminant Hepatic Failure", *J. Clin. Invest.*, vol. 81, Feb. 1988, pp. 414-419.

Takahashi et al, "Hepatocyte Growth Factor Is the Most Potent Endogenous Stimulant of Rabbit Gastric Epithelial Cell Proliferation and Migration in Primary Culture", *J. Clin. Invest.*, vol. 95, May 1995, pp. 1994-2003.

Huang et al, "Serum Hepatocyte Growth Factor Levels in Patients With Inflammatory Lung Diseases," Kaohsiung J. Med. Sci. 15:195-201, 1999.

Ueda et al, "Hepatocyte Growth Factor in Assessment of Acute Pancreatitis: Comparison With C-Reactive Protein and Interleukin-6," J. Gastroenterol, 1997; 32:63-70.

Matsuno et al, "Clinical Evaluation of Hepatocyte Growth Factor in Patients With Gastrointestinal and Pancreatic Diseases With Special Reference to Inflammatory Bowel Disease," Research Communications in Molecular Pathology and Pharmacology, vol. 97, No. 1, Jul. 1997, pp. 25-37.

Tsubouchi et al, "Levels of the Human Hepatocyte Growth Factor in Serum of Patients With Various Liver Diseases Determined by an Enzyme-Linked Immunosorbent Assay," Hepatology, vol. 13, No. 1, 1991, pp. 1-5.

Database Medline, U.S. National Library of Medicine (NLM), Bethesda, MD, US; Jul. 1998, Prokhorova M. N. et al: "[The use of noninvasive biological means in assessing lipids in children]", Database Accession No. NLM9742758, Klinicheskaia Laboratornaia Diagnostika, Jul. 1998, No. 7, Jul. 1998, pp. 13-15.

* cited by examiner

Day0  Day3  Day7

SYNERGETIC EFFECTS OF HGF AND ANTIBACTERIAL TREATMENT

This is a 371 national phase of PCT/SE01/01831, filed 28 Aug. 2001, and published as Publication No. WO 02/17964 on 7 Mar. 2002 in English.

FIELD OF THE INVENTION

The present invention relates to a composition and a method for treatment of injury caused or complicated by infections such as pneumonia, injuries in the respiratory organs caused by burns and/or infections and infected chronic leg ulcers in the patients suffering from diabetes, venous or combined venous/arterial insufficiency, wherein a therapeutically active amount of HGF (hepatocyte growth factor) and at least antibiotic agent to which the infection in question respond are administered to a mammal suffering from such injury. The present invention also relates to analysis of excrement with regard to HGF, as well as a kit for carrying out the analysis for the diagnosis of certain illness conditions where HGF has turned out to be an important factor.

THE BACKGROUND OF THE INVENTION

Hepatocyte growth factor, (HGF), is a protein expressed in the mesenchymal cells such as lung macrophages and fibroblasts, kupffer cells in the liver and leukocytes. HGF is a cytokine, which is secreted at cell damage and appears to have an importance for the regeneration of certain organs and for the healing of wounds. Chemically HGF is a glycoprotein, which first is synthesised as an inactive precursor. The precursor is cleaved to an active protein in the damaged organ via a particular activator. HGF binds to heparin, which seems to have importance for the activation of HGF and the binding to its receptor. The receptor binding HGF is c-MET. Since the c-MET-receptor only is down-regulated in damaged organ, it is only cells in these damaged organs that appear to respond on a HGF-receptor interaction.

HGF plays a important role in the cell-cell-interaction between mesenchyme cells and epithelium cells. Mesenchyme cells produces HGF which influences epithelial cells. The target cells of HGF are fully developed epithelial cells, wherein the most important cells are hepatocytes in the liver, epithelial cells in the proximal and distal tubuli in the kidney and type II epithelial cells in the lungs. HGF is regulated by TGF β (transfer growth factor β), which counteract the effects of HGF. HGF exhibits three effects on epithelial cells: mitogenic, motogenic and morphogenic effects. HGF acts both paracrine, ie., an effect on adjacent cells and endocrine, a long-distant effect, e.g. HGF is transported via blood from the lungs to for example the liver or the kidney.

HGF is formed and is present in high concentrations in the body at damage. Previous studies show a correlation between high serum concentrations of HGF and a good prognosis in pneumonia. The serum concentrations of HGF increase at acute infectious diseases. This has been registered via control of the concentrations of serum HGF in patients suffering from sepsis, pneumonia, infectious gastroenteritis, erysipelas, and urinary tract infections. The HGF values do not increase at chronic diseases, as well as at chronic hepatitis. This may be a reason for the formation of fibroses in such infections.

The effect of HGF has also previously been investigated on skin cells. The DNA synthesis is doubled in human skin fibroblasts after addition of more than 1.0 ng/ml of HGF to cultures media. The effect was inhibited using monoclonal antibodies against HGF.

The presence of chronic leg wounds in elderly patients and especially in the patients suffering from diabetes is a large problem in today's health care. These leg wounds depend on different causes such as inappropriate circulation and are therefore very difficult to heal. These patients usually suffer from venous insufficiency or combined venous and arterial insufficiency. At present, there is not any real satisfactory treatment. The methods available are time consuming, difficult and costly. The current methods include usage of a saline compress, enzymatic treatment using varidase to degrade fibrin, skin grafts and surgery of varix. These ulcers are nearly always contaminated by different bacterial flora. When the signs of infection are dominated the ulcers are treated by antibiotics according to the culture results. Though improvement of ulcer in general, the antibacterial treatment can seldom cure the ulcers.

During the course of pneumonia there are lots of patients, especially elderly, who do not recover in spite of successfully antibacterial treatment. This is the case in other serious lung injuries such as burn injuries that are complicated by infections.

Based on clinical studies the inventors mean that in such cases as mentioned before a combination of HGF local therapy and appropriate antibacterial treatment have synergetic effects that are considerably more than using either of the treatments alone.

SUMMARY OF THE INVENTION

The object of this invention is to provide a therapeutic composition for healing injuries that are caused or complicated by infections. The invention is based on a clinical study and observations of HGF (hepatocyte growth factor) in a composition for local treatment of ulcers in patients and inhalation administration in injuries in the respiratory organ in the course of pneumonia. This object has been solved due to the discovery that a synergetic effect exists between a HGF and a suitable antibiotic agent during treatment of complicated respiratory injuries and other infectious diseases such as pyelonephritis, endocarditis, meningitis and infectious colitis.

The invention provides a method for treatment of injury caused or complicated by infections such as pneumonia, injuries in the respiratory organs caused by burns and/or infections and infected chronic leg ulcers in the patients suffering from diabetes, venous or combined venous/arterial insufficiency, wherein a therapeutically active amount of HGF and at least antibiotic agent to which the infection in question respond are administered to a mammal suffering from such injury.

According to another aspect of the invention it also provides the use of a combination of HGF and at least one antibiotic agent for the preparation of pharmaceutical compositions for the treatment of an mammal suffering from an injury caused or complicated by infections such as pneumonia, an injury in the respiratory organs caused burns and/or infections and infected chronic leg ulcers in the patients suffering from diabetes, venous or combined venous/arterial insufficiency.

According to another aspect of the invention it also provides the use of HGF for the preparation of pharmaceutical composition for the treatment of an mammal suffering from an injury caused or complicated by infections such as pneumonia, an injury in the respiratory organs caused burns and/or infections and infected chronic leg ulcers in the patients suffering from diabetes, venous or combined venous/arterial insufficiency, wherein said mammal is subjected to at least one antibiotic agent to which the infection in question respond.

One aspect of the invention provides a pharmaceutical composition for the treatment of an injury caused or complicated by infections such as pneumonia, an injury in the respiratory organs caused by burns and/or infections and infected chronic leg ulcers in the patients suffering from diabetes, venous or combined venous/arterial insufficiency, comprising a therapeutically active amount of HGF and at least one antibiotic agent to which the infection in question respond.

Another aspect of the invention provides a kit for the treatment of an injury caused or complicated by infections such as pneumonia, an injury in the respiratory organs caused by burns and/or infections and infected chronic leg ulcers in the patients suffering from diabetes, venous or combined venous/arterial insufficiency, comprising a therapeutically active amount of HGF and at least one antibiotic agent to which the infection in question respond.

Yet another aspect of the invention provides a kit for determining HGF in excrement from a patient to determine an ongoing infection and/or ongoing treatment of such infection, comprising a HGF determinant.

The combination of HGF and the antibiotic agent used which is relevant for the infection in question accentuates process of healing dramatically and shortens the convalescence period. HGF can be used in acute, sub-acute as well as chronic injuries caused or complicated by infectious agents.

The invention also provides a method for diagnosis of an ongoing infection where HGF has turned out to be an important factor, wherein the excremental presence of HGF is determined.

DETAILED DESCRIPTION OF THE INVENTION

This invention is directed to a method of enhanced therapeutical effect of antibacterial treatment of complicated infectious diseases by simultaneous administration of HGF (hepatocyte growth factor). The inventors have discovered such a synergetic effect by clinical studies using HGF in treatment of chronic leg ulcers and pneumonia. Hence HGF can be used to enhance therapeutical effects of antibiotics in other infectious diseases such as pyelonephritis, endocarditis, meningitis that are followed by some extent of organ injuries in spite of successful antibacterial treatment.

The method according to the invention using a therapeutically active amount of HGF can be used in bacterial infection such as tuberculosis, un fungal infections as well as viral infections such as a complementary treatment.

The method can be used for treatment of injury caused or complicated by infections such as pneumonia, injuries in the respiratory organs caused by burns and/or infections and infected chronic leg ulcers in the patients suffering from diabetes, venous or combined venous/arterial insufficiency. A therapeutically active amount of HGF and at least antibiotic agent to which the infection in question respond are administered to a mammal suffering from such injury. The mammal in question can be a human but it may also be a domestic animal such as a horse, a cow or a sheep or a pet such as a cat.

The antibiotic agent can be an antibacterial agent or fungicide. HGF and the antibiotic agent can be in the same pharmaceutical composition or in the different pharmaceutical compositions and HGF can be administered before, during or after the anti-infectious treatment.

Said composition comprising HGF can be administered topically, intravenously, intramuscularly, subcutaneously, via inhalation, intrathecally or per rectally. Said composition can comprise native mammalian HGF, but it may also comprise recombinant HGF, as well as a polypeptide exhibiting a HGF activity. The composition may also comprise transfected cells expressing HGF. HGF can further be administered i combination with heparin or low molecular heparin such as fragmin.

The present invention further provides the combination and the use of a combination of HGF and at least one antibiotic agent for the preparation of pharmaceutical composition for the treatment of an mammal suffering from an injury caused or complicated by infections such as pneumonia, an injury in the respiratory organs caused burns and/or infections and infected chronic leg ulcers in the patients suffering from diabetes, venous or combined venous/arterial insufficiency. The antibiotic agent itself and the dose of said antibiotic agent is chosen so that it responds to the infection in question. HGF and the antibiotic agent can be in the same pharmaceutical composition or in the different pharmaceutical compositions as a kit. HGF can be administered before, during or after the anti-infectious treatment. For a local administration a suitable dose of HGF will be about 0.5-20 ng/cm$^2$ of the surface to be treated.

At local HGF treatment, complete or partial healing was seen in 8/11 patients with chronic leg ulcers which had been incurable for up to fourteen years (Example 2, Table 1). A composition of HGF was used in the treatment of chronic leg ulcers, which had failed to be treated in spite of several attempts during a long time. In all of the cases a bacterial flora was discovered by cultures prior to treatment. The best results were seen in the apparently infected ulcers, which were treated simultaneously by representative antibiotics. Treatment of patients with appropriate antibiotics (in these cases orally) at the same time as HGF treatment (locally) resulted in a faster improvement that ultimately resulted in complete cure of ulcers in at least 4 cases. The new skin had a fine quality and the patients did not have the ulcers back up to one year of control. Local treatment by HGF seemed to have positive effect on nearby, not locally treated ulcers indicating systemic effects. No signs of allergy or malignancy were observed during one year of observation. HGF and representative antibacterial treatment have synergetic effects in treatment of chronic leg ulcers. Micro-circulatory perfusion, which might reflect the angiogenic effect of HGF was controlled by a Laser Doppler method and showed a significant positive correlation to ulcer area reduction.

Figure 2:
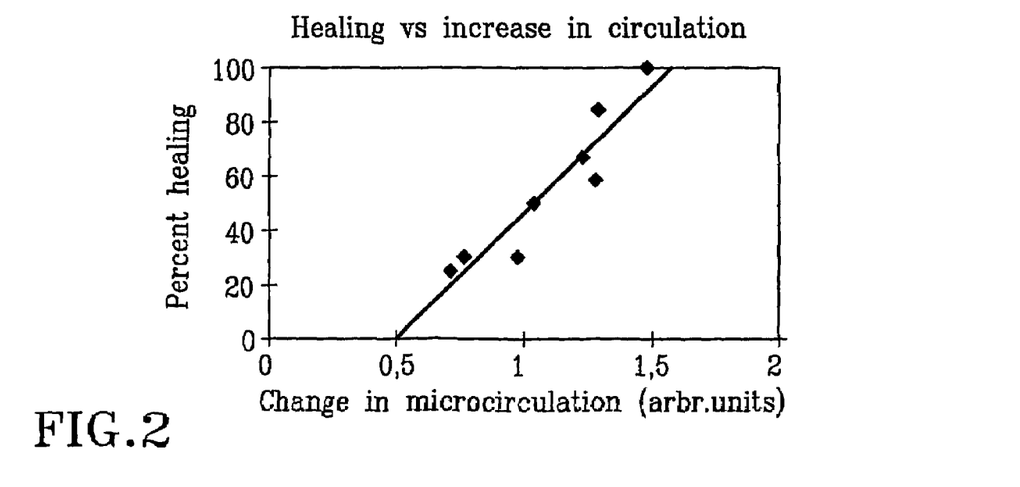
FIG. 2: The correlation between micro-circulatory perfusion and ulcer area reduction after local HGF application. The relationship between change in micro-circulatory perfusion one week after treatment start (>1 indicates increase) and ulcer area reduction (% healing) up to three months.

In one patient with venous insufficiency who had recovered considerably after one week a superinfection with resistant bacteria was observed. This patient could not be treated by appropriate antibiotics due to allergy to penicillin and the ulcer increased dramatically in size in spite of attempts with HGF. Micro-circulation controls by Doppler-laser confirmed increased levels in the successfully treated ulcers but not in the ulcers that failed to improve by HGF treatment or in the case of relapse after failure in antibacterial therapy (Table 1, FIG. 2).

Angiogenesis is a known effect of HGF treatment and this might be the cause of increased micro-circulation in the successfully treated ulcers. However we believe that bacteria overgrowth may spread to the vascular channels and cause necrosis in the wound. Eradication of bacteria by effective antibacterial treatment causes increased microcirculation as well. The synergetic effects of HGF and antibiotics accelerate the therapeutical efficacy of treatment considerably. This was also shown in one patient with a large progressing ulcer on the leg with necrosis in the surrounding skin (see example 7).

Figure 1:
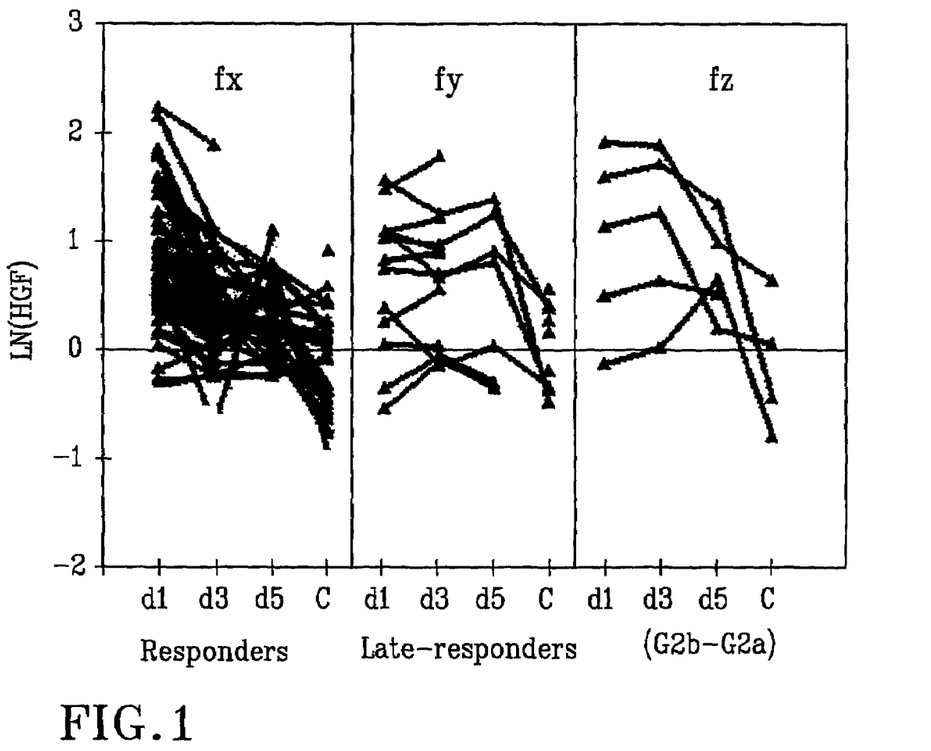
FIG. 1: Hepatocyte growth factor levels during treatment of pneumonia in responders and late-responders. Changes in serum HGF levels during treatment (Day 1-5; d1, d3, d5) and at convalescence (C) in responders (fx) and late-responders (fy respective fz). G2b and G2a respectively: Late-responders' subgroups consisting of the patients who changed their treatment to appropriate one after Day 5 respective at Days 3-5.

The patients with pneumonia have high serum HGF levels. In the patients with low acute serum HGF levels an unfavourable outcome not proportional to the choice of antibacterial therapy was observed (Scand J Infect Dis; 30: 405-9, 1998). The inventors have followed the serum HGF levels in the patients with pneumonia while treated on ward, before and after treatment and have shown that serum HGF levels followed sensitively the antibacterial effects of initiated therapy. The serum levels of HGF decreased by effective therapy (FIG. 1).

According to the level and velocity of changes it was possible to guess the efficacy of the chosen antibacterial treatment which agreed to the clinical status in the patient. The eradicating of bacteria by antibiotics might have put out the inflammatory responses in the body, which may have been followed by rapid changes in systemic HGF production and release. In the patients who were not treated by the representative antibiotics the serum HGF increased until the proper therapy was initiated.

These studies prepared us to realise the mutual effects of antibacterial treatment and HGF levels during infectious diseases such as pneumonia.

Figure 3:
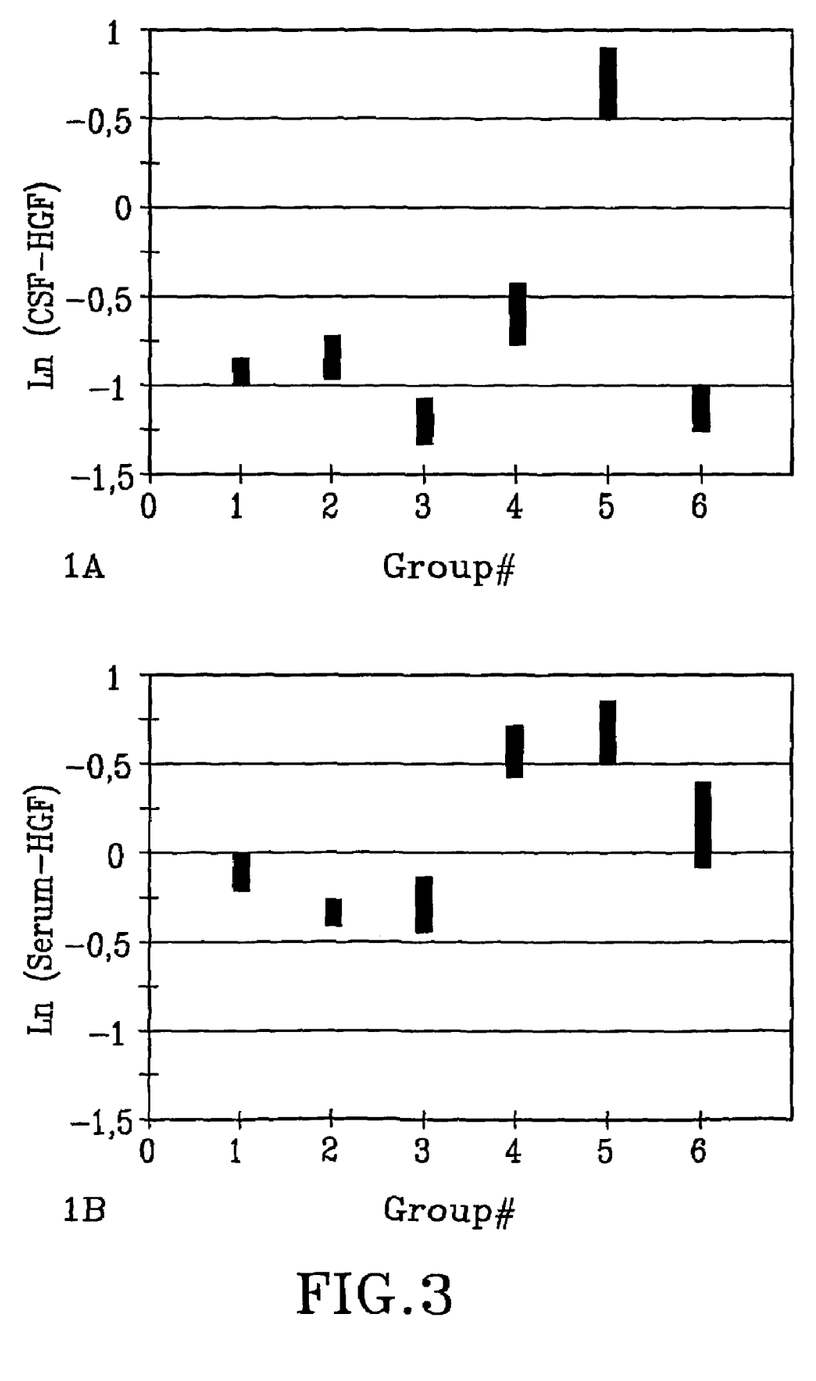
FIG. 3: Serum and cerebro-spinal concentrations of HGF in different patient groups Group mean values (±SEM) of HGF-CSF (1A) and serum HGF (1B) expressed as the natural logarithm, ln. (Group 1-6; facialis pares, Borrelia meningitis, viral meningitis, Herpes encephalitis, bacterial meningitis and control group)

We have observed that a local production of HGF happens at the same time as a systemic release of HGF during infectious diseases. A local production of HGF in cerebro spinal fluid (CSF) during bacterial meningitis was observed (J Infect Dis 2000; 181: 2092-4) (FIG. 3).

Figure 4:
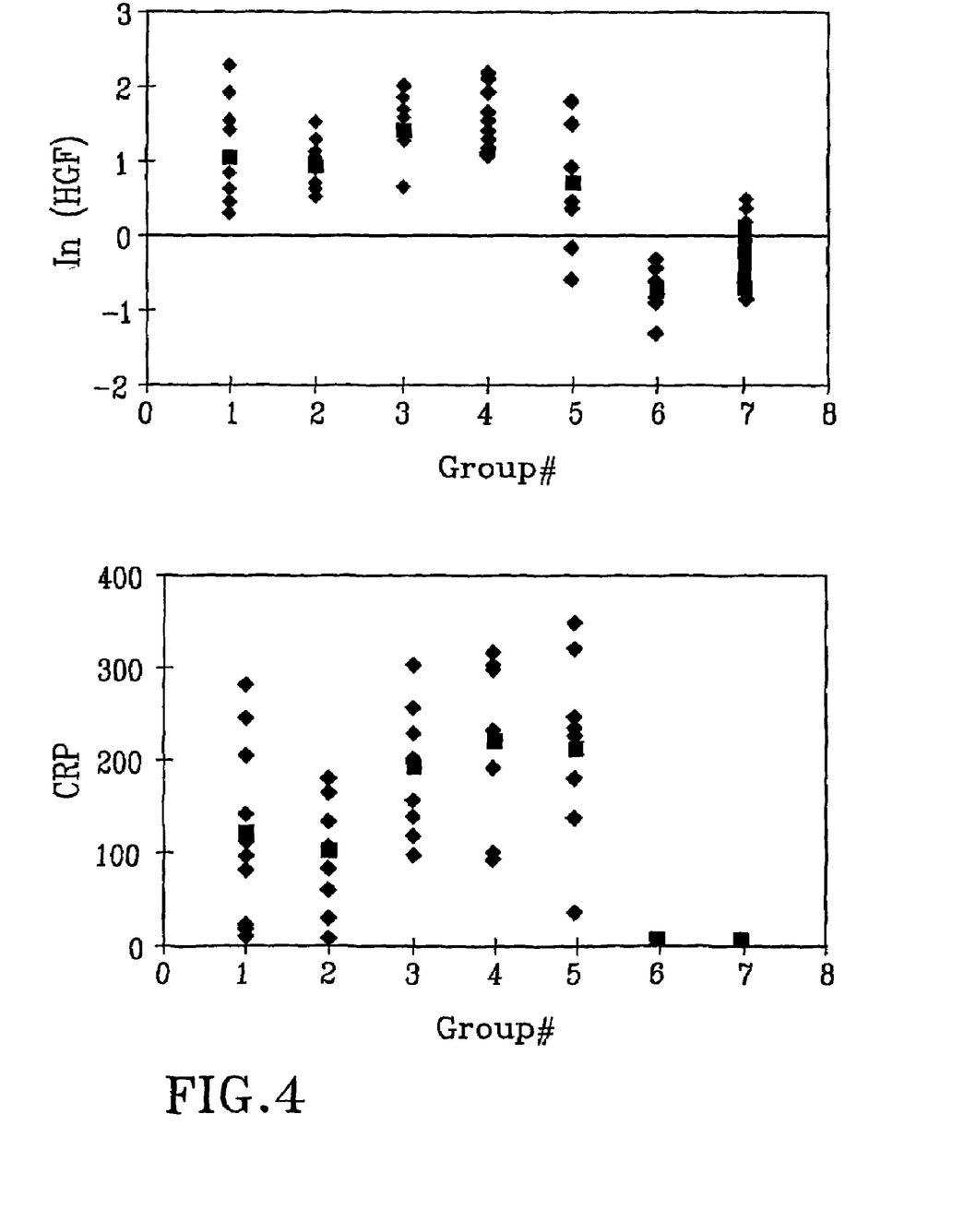
FIG. 4: Serum concentrations of HGF during infectious diseases Individual values (diamonds) of (1a) the natural logarithm (ln) of serum HGF concentrations and (1b) CRP concentrations (mg/ml) and corresponding mean values (filled squares) in different groups (Group 1-7; gastroenteritis, erysipelas, pyelonephritis, septicaemia, pneumonia, chronic hepatitis and a reference group)

The inventors have shown that serum HGF levels increase in other infectious diseases such as gastroenteritis, erysipelas, septicemia, infectious colitis and pyelonephritis (FIG. 4). A synergetic effect might exist in treatment of other serious infectious diseases with HGF and antibiotics.

An in vivo example of the synergistic effect of HGF and an antibiotic agent, is an old patient suffering from pneumonia subsequent respiratory insufficiency. He was given a single dose of HGF during treatment of an antibiotic agent which lead to a rapid recovery as described in example 8.

The inventors have shown by clinical studies and case reports the close relationship between bacterial eradication and regeneratory effects of HGF on healing of injuries caused or complicated by infections.

The present invention provides a kit for determining HGF in excrement from a patient, wherein excrement shall mean in exhalation air, in serum, in faeces, in urine or the like. The kit contains means for the determination of an ongoing infection and/or ongoing treatment of such infection, comprising a HGF determinant. The kit also comprises either a means for collecting and freezing exhalation air or a means for collecting and freezing faeces or means for collecting faeces or means for collecting urine.

In the method according to the present invention for diagnosis of an ongoing infection, the excremental presence of HGF is determined. The term "exkremental presence of HGF" in this description includes the presence of HGF in exhalation air, in serum, in faeces, in urine or the like.

HGF is produced after injuries and is detected in increased amounts in serum during acute inflammatory diseases. Lung is one of the major sources of HGF. HGF m-RNA has been found in alveolar macrophages indicating a local production in the airway. By cooling exhaled air a condensate is formed containing molecules from bronchi and alveoli. A study was performed if HGF could be found in exhaled breath condensate (EBC) and to investigate its concentration and time course in pneumonia, (see example 9). Results showed the concentrations of HGF were significantly higher both in serum and in EBC in patients with acute pneumonia. High serum HGF-levels that was observed at the acute phase of pneumonia dropped significantly within 48 hours after effective antibiotic treatment. Following serum HGF-levels before and within 48 hours of treatment might predict the therapy results more reliably than CRP (C-Reactive Protein). Further studies are going on that show a significant decrease in serum HGF within 24 hours of initiating the appropriate antibiotic in pneumonia. Thus determination of serum HGF might predict the therapy results as soon as within 24 hours of treatment when neither temperature, $O_2$ saturation, CRP nor other markers are capable of predicting the therapy results.

Increased production of HGF takes place both systemically and locally at infections. It has been shown that intrathecal production of HGF takes place in liquor at acute meningitis. High concentrations of HGF reflects the attempt of the body to carry out ulcer healing and that low concentrations of HGF at infections, such as pneumonia, (in spite of increasing CRP), can be connected to a bad prognosis. Serum HGF values at pneumonia has been followed during the course of the treatment and it has been noticed that HGF an be used as a marker for efficiency of treatment of pneumonia.

Serum and faeces concentrations of HGF in patients suffering from acute gastroenteritis was performed (see example 10), showing that the HGF concentration in serum increased and in faeces a dramatic increase in HGF levels was observed that decreased to a level comparable to faeces HGF in healthy controls at convalescence. HGF levels in faeces in the patients with infectious gastroenteritis was significantly higher ($p<10^{-9}$) than patients with inflammatory bowel disease as well as patients with culture negative diarrhea ($p<10^{-7}$).

The method and the corresponding kit can be used in other infections as well, such as meningitis, urinary tract infections, erysipelas where high values of HGF both in serum and faeces have been determined, as well as locally at the infection. This makes HGF to a good marker to determine an ongoing infection or to check if a antibiotic treatment really works.

The invention is further described in the following non-limiting examples.

EXAMPLE 1

HGF as a Therapeutic Predicator in Pneumonia

In a prospective study the serum values of HGF were measured in the patients with pneumonia within 24 hours (n=70), after 3 (n=70) and 5 days (n=47) and finally after 4-6 weeks (n=46). An enzyme-linked immuno-sorbent assay (ELISA) was performed. A commercially available ELISA kit (Quantikine HGF Immunoassay, R&D systems Inc., Minneapolis, USA) has been used. The patients were classified into responders and late-responders on clinical grounds and without knowledge of the HGF values.

It was found that serum HGF levels initially were high in all patients. The responders exhibited successively lower HGF levels during treatment on ward with normal values in the convalescent period (p<0.0001). In the late-responders the levels remained unchanged or increased and did not decrease (ANOVA; n=70; p<0.0005) until the appropriate treatment was initiated. The HGF levels followed sensitively the anti-bacterial choice.

Measuring HGF might give important information about the regeneratory status, which in turn corresponds to the clinical outcome in pneumonia.

EXAMPLE 2

Hepatocyte Growth Factor Accelerates Healing in Chronic Leg Ulcers

A gel containing HGF and heparin was prepared as follows:

| Preparation 1: Sterile PBS solution containing polysorbat 80 | |
|---|---|
| Potassium chloride | 0.20 g |
| Monopotassium phosphate | 0.20 g |
| Disodium dihydrogen phosphate | 1.40 g |
| Sodium chloride | 8.00 g |
| Polysorbat 80 | 50 mg |
| Water to | 1000 ml |

Preparation 1 can be prepared in advance and be dispensed in 100 ml injection bottles.

| Preparation 2: Sterile PBS gel | |
|---|---|
| Hypromellos | 20.0 g |
| Preparation 1 | to 1000 ml |

Preparation 1 and 2 can be prepared in advance and be dispensed in 100 ml injection bottles. The following preparations 3 to 5 are prepared just before the usage of the same.

| Preparation 3: Diluent fluid | | |
|---|---|---|
| Albumin | (200 mg/ml, Pharmacia & Upjohn) | 25.0 ml |
| Heparin | (25.000 IE/ml, Lövens) | 0.8 ml |
| Preparation 1 to | | 1000 ml |

| Preparation 4: HGF solution | |
|---|---|
| Hepatocyte growth factor (HGF) | 10 µg |
| Preparation 3 to | 100 ml |
| giving 100 ng HGF per ml | |

In order to prepare HGF preparations, recombinant human HGF (rhHGF) was provided commercially from R&D systems Inc., Minneapolis, USA.

A Millex Durapore® filter (Millipore) is saturated by pressing 20 ml of Preparation 3 through the filter. Preparation 4 is sterile filtered through the saturated filter. The filtrate is dispensed in 10 ml injection bottles and is frozen.

Preparation 5: HGF Gel 90 ml of Preparation 2 is measured into a sterile ointment dish. The addition of 10 ml fresh thawed Preparation 4 takes place to the gel, giving a concentration of (10 ng HGF/ml). Mixing and dispensing to preferably a 10 ml injection syringe that is sealed using a lid of a known kind.

HGF in gel form was applied locally once daily for seven days in 15 of 19 chronic leg ulcers in eleven elderly patients in a pilot study. All patients had previously been treated with conventional methods and their leg ulcers had been in a rather stable condition for between one and fourteen years. Any signs of allergy, discomfort or pain were reported daily.

The micro-circulation within the ulcers was measured using LDPI. The LDPI system (PIMLO, Lisca Development AB, Sweden) utilises the Doppler principle by freely impinging coherent laser light onto the tissue and processing the backscattered, Doppler broadened, light to estimate the tissue perfusion without touching the skin. The perfusion estimate is proportional to the product of the mean velocity and the concentration of the moving blood cells. The estimate does not provide an absolute perfusion measurement but rather a relative value.

Micro-circulation perfusion in ulcers compared to the intact contiguous skin was determined at the beginning, after one week and after three months (in 7 patients) and ulcer size and characteristics were also documented.

Complete healing (100% area reduction) was seen in 5/15 ulcers in three patients, excellent healing (84-99%) in four ulcers in another four patients and favourable healing (58-59%) in two ulcers. Minimal improvement (25-30%) or relapse were observed in the remaining four ulcers (three patients). In the four contiguous non-treated ulcers (two patients), three healed completely and one excellent. In contrast to the patients with unfavourable healing (non-responders) the healing process in the responders began during treatment and continued afterwards. There was a statistically significant correlation (r=0.94, p<0.002) between enhanced micro-circulation and ulcer area reduction in the treated ulcers. Simultaneously antibacterial treatment in the ulcers with signs of infection enhanced the therapy results considerably. Thus at local HGF treatment, complete or partial healing was seen in 8/11 patients with chronic leg ulcers which had been incurable for up to fourteen years. Micro-circulatory perfusion, which might reflect the angiogenic effect of HGF, was positively correlated to ulcer area reduction. Local treatment by HGF seems to have positive effect on nearby, not locally treated, ulcers indicating systemic effects. No signs of allergy or malignancy were observed during three months observation. HGF and representative antibacterial treatment have synergetic effects in treatment of chronic leg ulcers.

nant human HGF (rhHGF) was provided commercially from R&D systems Inc., Minneapolis, USA. Group 2 (n=6 males) received 0.35 µg/kg/day (5-10 ng/cm² hairless skin) on the right side in 10 days. Group 3, non-treated, served as the control group. None of the treated animals did show any sign of non-tolerance or diseases under or after course of treatment. Although some significant differences were not obviously seen in the hair growth under treatment we were sur-

TABLE 1

| Pat # | Age (yrs) | Type | Ulcer (yrs) | age T/NT (#) | Treated ulcers | | | | Non-treated ulcers | | | |
|---|---|---|---|---|---|---|---|---|---|---|---|---|
| | | | | | Loc (T) | Area (T) cm² | Circ (T) ratio | Heal % (T) | Loc (NT) | Area (NT) cm² | Circ (NT) ratio | Heal % (NT) |
| 1 | 86 | vi | 1 | 2/0 | LMdx/LMsin | 1.3 | ND | 100 | | | | |
| 2** | 92 | vi | 1.5 | 1/0 | Leg sin | 306 | ND | 100 | | | | |
| 3** | 82 | vi + ai | 14 | 2/2 | MMdx/MMsin | 14 | 1.48 | 100 | LMsin/LMsin | 11.20/5.95 | 2.88/ND | 100/92 |
| 4** | 76 | vi | 1.5 | 1/0 | Heel sin | 0.5 | ND | 99 | | | | |
| 5** | 60 | vi | 5.5 | 1/0 | Leg dx | 40 | ND | 99 | | | | |
| 6 | 75 | diab | 1.5 | 1/0 | MMdx | 15 | 1.29 | 84 | | | | |
| 7 | 86 | vi | 1.5 | 2/0 | MMdx/MMsin | 21 | 1.23 | 67 (59-88%)♦ | | | | |
| 8** | 88 | vi | 5.5 | 1/2 | MMdx | 9 | 1.28 | 58 | LMdx/LMdx | 1.0/0.12 | 0.65/ND | 100/100 |
| 9*** | 75 | vi | 5.5 | 2/0 | MMsin/LMsin | 28 | 0.77 | 30 | | | | |
| 10 | 96 | ai | 1.5 | 1/0 | Leg dx | 26 | 0.72 | 25 | | | | |
| 11** | 73 | vasc | 5.5 | 1/0 | Leg sin | 96 | 0.97 | 30 | | | | |
| total | | | | 15/4 | | | | | | | | |
| Mean | 80.8 | | 4.0 | | | 51 | 1.12 | 78* | | 6.10/3.04 | 0.9/ND | 100/96 |
| Median | 82.0 | | 1.5 | | | 21 | 1.23 | 84 | | 6.10/3.04 | 0.9/ND | 100/96 |

Patient data, leg ulcer classification and result of local HGF treatment for seven days. Ulcer type: vi and ai = venous and arterial insufficiency, respectively, diab = diabetic ulcer and vasc = vasculitis. T/NT (#) is number of locally treated (T) and non-treated (NT) ulcers in each patient. Data from treated ulcers are shown in the middle section and data from not-treated ulcers in the right section. Loc is location (LM and MM are the lateral and medial malleolus,respectively, dx and sin are right and left leg respectively. Area (cm²) is the total ulcer area (all treated ulcers in patient) and circ is the relative change in local microcirculation, expressed as the ratio of skin blood perfusion before treatment and one week later (ND = not done). Heal % is ulcer area reduction up to three months (all treated ulcers in patient). *sum of total area reduction divided by sum of total area.the patients who received representative antibiotics under treatment. *therapy failure because of resistant bacteria ♦this patient had two ulcers with different healings procent.

EXAMPLE 3

Increased Serum Levels of HGF in the Patients with Acute Infectious Diseases.

In a prospective study we have measured the serum HGF levels from patients with different infectious diseases and from healthy adults and elderly. An enzyme-linked immunosorbent assay (ELISA) method was used. Six clinical groups were identified (n=10 in each group): gastroenteritis, skin and soft tissue infection, urinary tract infection, septicemia, pneumonia, and chronic hepatitis C. Seventy-five healthy persons served as a control group. We found higher levels of HGF in the sera from patients with acute infectious diseases (Group 1-5) compared to the healthy population as well as compared to the patients with chronic hepatitis C ($p<0.0001$). CRP and HGF were highly correlated ($r=0.65$). We conclude that HGF rises in serum from patients with acute infectious diseases but possibly not in chronic infections.

EXAMPLE 4

The Effects of Recombinant Human HGF (rhHGF) on Normal Hairless Skin in Mice.

Eighteen black mice (14-16 weeks old and 21-29 g weight) were shaved on their back, causing two 1×1 cm patches on the right and left side. They were then divided into 3 groups. Group I (n=6, females), Group 2 (n=6 males) and Group 3 (n=6, 3 males and 3 females). Group 1 were treated locally on the right side by 0.70 µg/kg (12-18 ng/cm² hairless skin) recombinant human hepatocyte growth factor (rhHGF) daily in 10 days. In order to prepare HGF preparations, recombiprised to see that the animals in Group 1 did show a full double-sided hair growth in 5 animals 2 days after the treatment was ended (day 12). The same process in Group 2 and group 3 did take much a longer time (day 20 and day 21, respectively). Obviously though the animals in Group 2 showed an increased hair growth on the right side between day 15 and day 18 of treatment there was no significant differences between this group and Group 3 according to the time it took for them to show a full double-sided hair growth.

Figure 6:
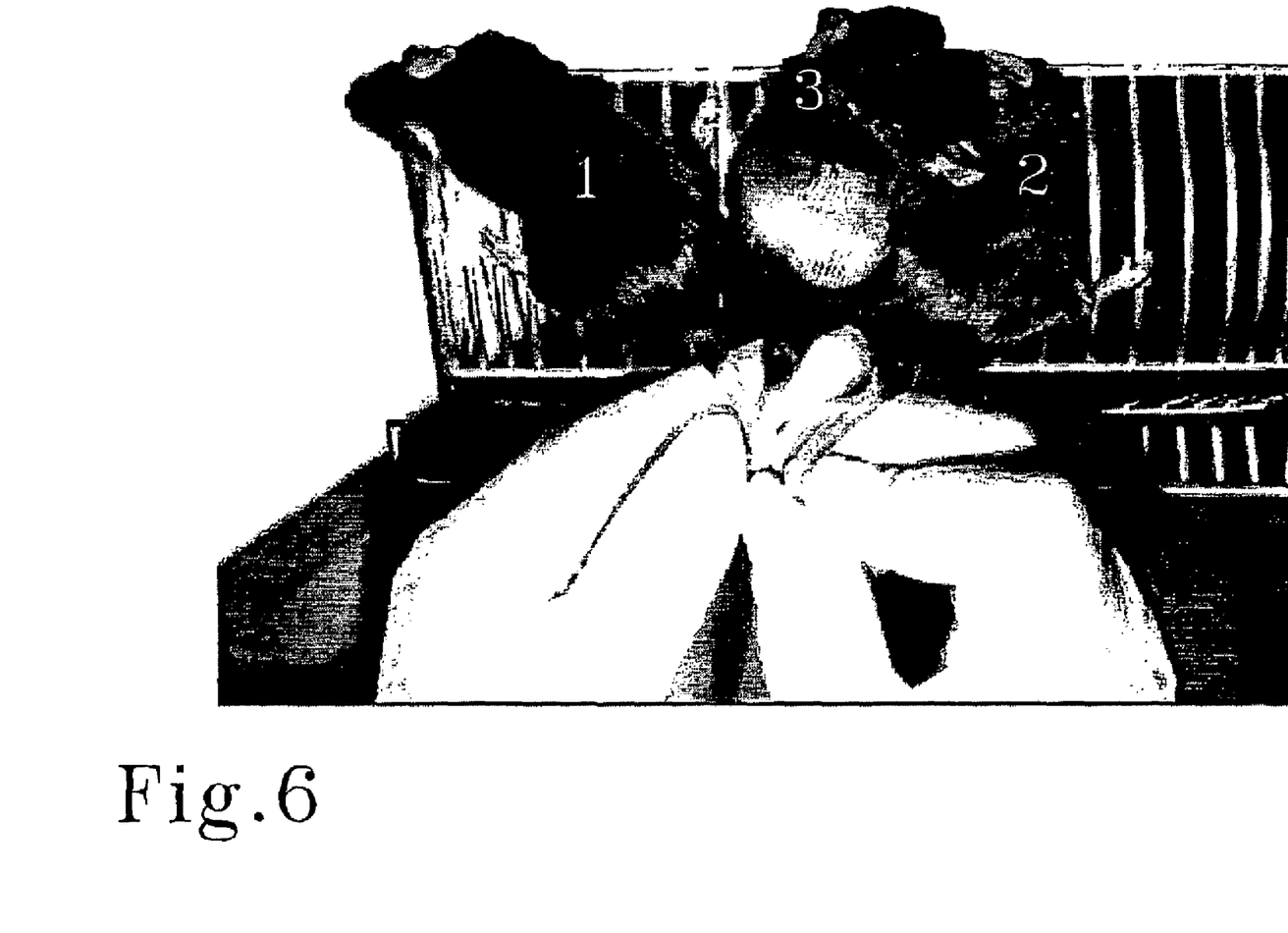
FIG. 6: Mice treated locally with HGF on the shaved skin in 10 days. The picture is taken 12 days after therapy started. 1: Mouse treated with 0.75 µg/kg/day in seven days. 2: Mouse treated with 0.35 µg/kg/day. 3: Control mouse

We conclude that local treatment of the normal, hairless skin in mice in the doses not less than 0.7 µg/kg accelerates the hair growth and this local treatment is tolerated by animals without problem (see FIG. 6).

EXAMPLE 5

Figure 7:
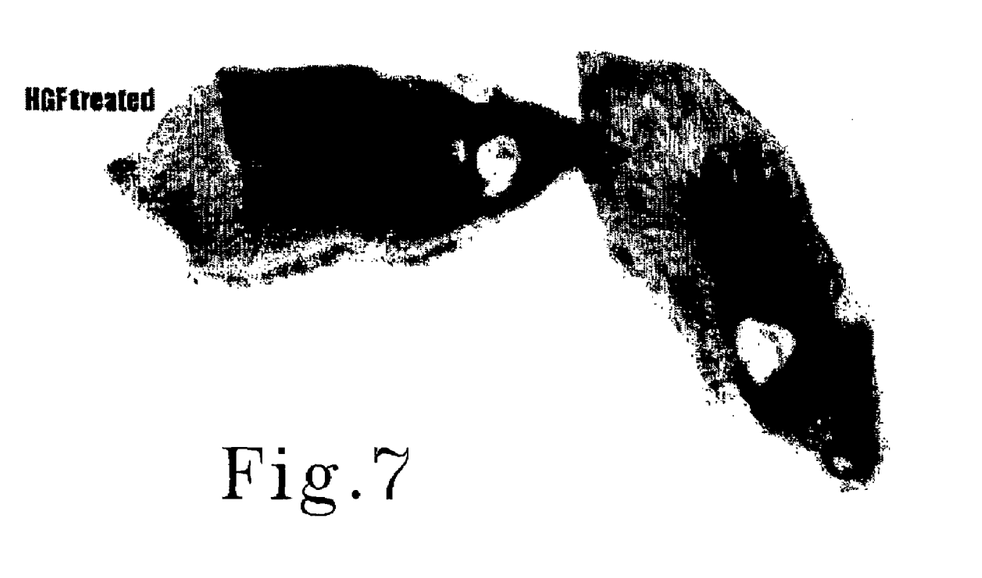
FIG. 7: Mice with fungal infection on their back one of which has been treated by HGF at the same time as local anti-fungal treatment. Note the difference in hair growth at the place of HGF treatment.

Two mice (23-25 g) with spontaneous fungal infections and ulcers on their backs were shaved and treated locally with Gentiana violet once. One of them was simultaneously treated with hepatocyte growth factor (rhHGF) 10 ng subcutaneously. The hair growth was fine as in the other places of body, in the mouse that received HGF and fungicidal treatment. In the other mouse the hair growth was rough and irregular although the hair growth was completed at the same time as the other mouse. This example confirms the morphogenic effects of HGF in recovering after treated infectious injuries (see FIG. 7).

EXAMPLE 6

The confluent monolayer of CCL-53.1 was scraped off, forming long wounds. The area not covered by cells finally disappeared, and restitution (in control medium with 15% horse serum and 2.5 % FBS) was completed at 72 h. The addition of HGF together with the addition of antibiotic agent (streptomycin and penicillin) to the culture medium improved the restitution of the damaged area more rapidly than the control medium (10 times at 24 h) as well as to a medium including HGF without added antibiotic agents. The effect exhibits a dose-dependency and is detectable using HGF in a concentration of ≧5 ng/ml.

EXAMPLE 7

The Synergetic Effects of HGF and Antibiotics on a Patient Having Leg Ulcers

Figure 5:
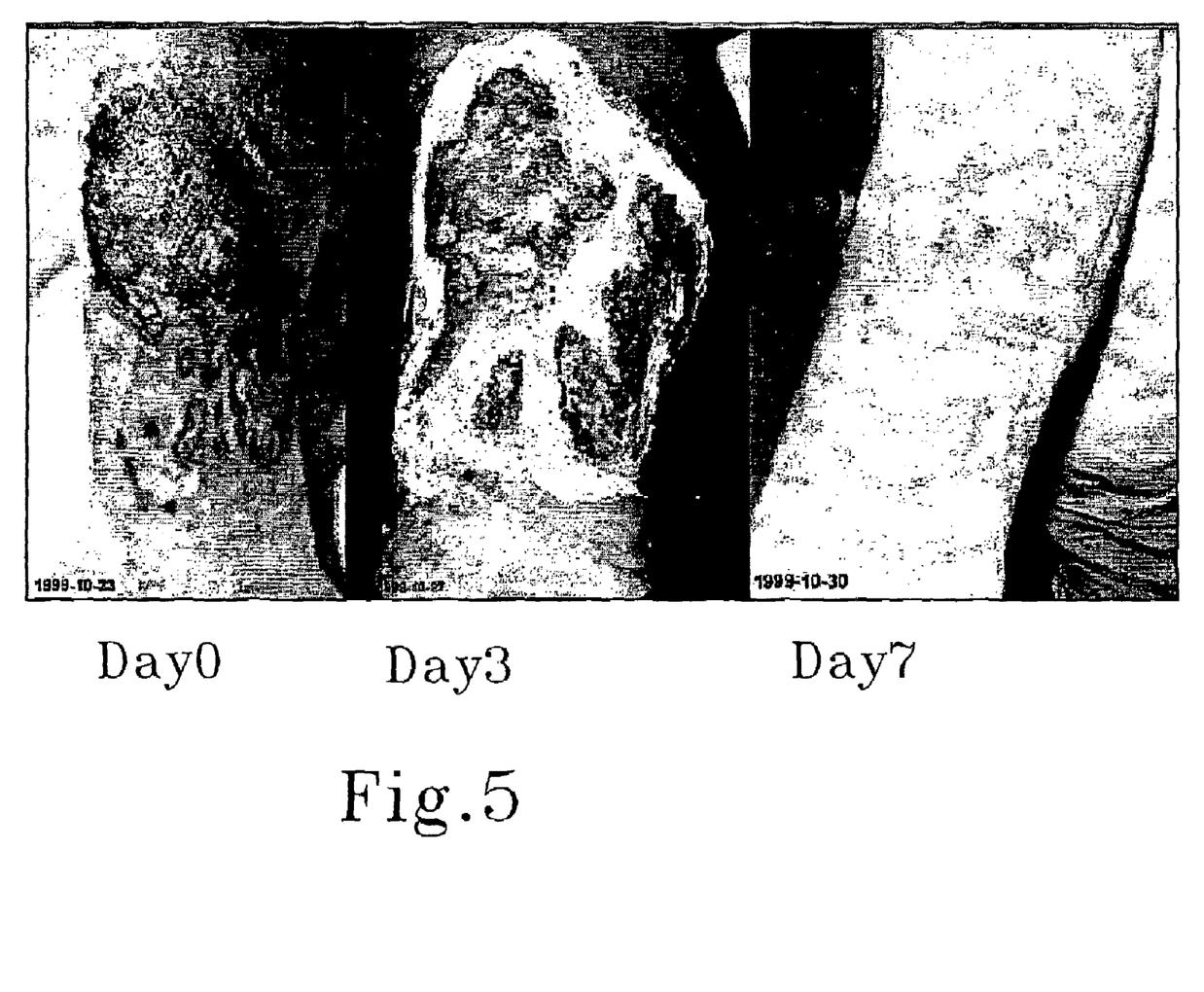
FIG. 5: Chronic ulcer treated in one week in a 91 years old woman.

A combination of HGF and antibiotics accelerate the therapeutical efficacy of treatment considerably. This was shown in one patient with a large progressing ulcer on the leg with necrosis in the surrounding skin. The cultures from the ulcer yielded growth of Staphylococcus aureus and the patient was treated by flucloxacillin in 10 days prior to HGF treatment. The antibiotic treatment was discontinued and new cultures were taken that confirmed the previous results. The patient was then treated by a combination of HGF in gel form and antibiotics. The necrosis disappeared the next day after treatment and the ulcer was completely healed within 2 weeks, (see FIG. 5)

EXAMPLE 8

The Synergetic Effects of HGF and Antibiotics on a Patient Suffering from Pneumonia An old patient with pneumonia caused by Streptococcus pneumonia had been treated by antibiotics in 10 days and in spite of decreasing temperature and c-reactive protein (CRP) levels was in need of extra oxygen because of respiratory insufficiency. He was treated once by HGF solution that was inhaled by an apparatus. He recovered considerably the next day and left the hospital on the third day.

| A suitable composition for the inhalation of HGF | |
|---|---|
| recombinant HGF | 100 ng, |
| sodium chloride | 0.9%, |
| heparin | 250E |
| to 1 ml. | |

EXAMPLE 9

Exhaled Breath Condensate and Levels of HGF in Pneumonia

Hepatocyte growth factor (HGF) is a protein that is produced after injuries and is detected in increased amounts in serum during acute inflammatory diseases. Lung is one of the major sources of HGF. HGF m-RNA has been found in alveolar macrophages indicating a local production in the airway.

By cooling exhaled air a condensate is formed containing molecules from bronchi and alveoli. We wanted to study if HGF could be found in exhaled breath condensate (EBC) and to investigate its concentration and time course in pneumonia.

Paired serum and EBC was collected from 10 patients with pneumonia, 10 patients with other infectious diseases and 10 healthy personal. Concentrations of HGF were significantly higher both in serum and in EBC in patients with acute pneumonia than in the two control groups. A significant decrease in serum concentration was seen already after 4-7 days, whereas the elevated HGF levels of EBC persisted even after 4-6 weeks. These results might strengthen the notion of a local production of HGF and a long repair and healing process after pneumonia.

Increased production of HGF takes place both systemically and locally at infections. It has been shown that intrathecal production of HGF takes place in liquor at acute meningitis. High concentrations of HGF reflects the attempt of the body to carry out ulcer healing and that low concentrations of HGF at infections, such as pneumonia, (in spite of increasing CRP, C-Reactive Protein) can be connected to a bad prognosis. Serum HGF values at pneumonia has been followed during the course of the treatment and it has been noticed that HGF an be used as a marker for efficiency of treatment of pneumonia.

EXAMPLE 10

Serum and Faeces Concentrations of HGF in Patients Suffering from Acute Gastroenteritis A new study of the concentrations of HGF in serum and faeces of patients suffering from infectious gastroenteritis (acute and during the course of the disease). The aim is to monitor the acute values of HGF of patients suffering from gastroenteritis of different genes, how the HGF values differ during the period of disease at self-healing infections and, if antibiotics can influence the concentrations of HGF.

60 patients suffering from acute gastroenteritis were included in the study. Venous blood was collected from the patients within 24 hrs after hospitalisation and then daily for three days (72 hrs), after a week, and at next revisits and deep frozen directly upon collection. An ELISA method was used for determining HGF in serum. A modified method is used for determining HGF in faeces. Common blood samples and culture of faeces and PCR diagnostics to determine virus influenced gastroenteritis was carried out for all patients. It was determined that HGF values (concentration) in serum and faeces increase in patients suffering from acute gastroenteritis, but there are no studies having studied HGF during the course of the disease of these patients. The concentration of HGF per gram of faeces is at least 20 times higher in patients having a positive faeces culture than in patients having a negative faeces culture.

The invention is not limited to the above mentioned embodiments but shall be interpreted within the scope of the appending claims.

The invention claimed is:

1. A method of treating a chronic skin ulcer of a mammal, comprising providing an antibiotic or fungicide, and HGF to said mammal.

2. The method of claim 1, further comprising identifying the presence of bacterial flora in the chronic skin ulcer.

3. The method of claim 1, wherein said HGF is provided in a topical formulation.

4. The method of claim 3, wherein said topical formulation of HGF comprises a native mammalian HGF.

5. The method of claim 3, wherein said topical formulation of HGF comprises a recombinant HGF.

6. The method of claim 3, wherein an antibiotic is provided to said mammal.

7. The method of claim 6, wherein said antibiotic is provided in a topical formulation.

8. The method of claim 1, wherein an antibiotic is provided orally to said mammal.

9. The method of claim 1, further comprising providing heparin to said mammal.

10. The method of claim 1, wherein said HGF is native mammalian HGF.

11. The method of claim 1, wherein said HGF is a recombinant HGF.

12. The method of claim 1, wherein said HGF is provided by transfected cells expressing HGF.

13. The method of claim 1, wherein said mammal is a human.

14. The method of claim 1, wherein said chronic skin ulcer is a chronic leg ulcer and an antibiotic is provided.

15. A method of treating a mammal with a chronic skin ulcer, comprising:
   identifying a mammal with a chronic skin ulcer as one in need of an antibiotic and HGF; and
   providing to said identified mammal an antibiotic and HGF.

16. The method of claim 15, further comprising identifying the presence of bacterial flora in said chronic skin ulcer.

17. The method of claim 15, wherein said HGF is provided in a topical formulation.

18. The method of claim 15, wherein said antibiotic is provided in a topical formulation.

19. The method of claim 15, wherein said antibiotic is provided orally to said mammal.

20. The method of claim 15, further comprising providing heparin to said mammal.

21. The method of claim 15, wherein said HGF is native mammalian HGF.

22. The method of claim 15, wherein said HGF is a recombinant HGF.

23. The method of claim 15, wherein said HGF is provided by transfected cells expressing HGF.

24. The method of claim 15, wherein said mammal is a human.

25. The method of claim 15, wherein said chronic skin ulcer is a chronic leg ulcer.

* * * * *